United States Patent [19]
Lafontaine et al.

[11] Patent Number: 5,665,103
[45] Date of Patent: Sep. 9, 1997

[54] STENT LOCATING DEVICE

[75] Inventors: Daniel M. Lafontaine, Plymouth; Roger N. Hastings, Maple Grove, both of Minn.

[73] Assignee: SCIMED Life Systems, Inc., Maple Grove, Minn.

[21] Appl. No.: 612,158

[22] Filed: Mar. 7, 1996

[51] Int. Cl.$^6$ ............................................. A61M 29/00
[52] U.S. Cl. ..................... 606/192; 606/198; 606/194
[58] Field of Search ............................. 606/192, 194, 606/198, 195, 108; 623/1, 43

[56]  ' References Cited

U.S. PATENT DOCUMENTS

| | | |
|---|---|---|
| 3,661,148 | 5/1972 | Kolin . |
| 4,522,205 | 6/1985 | Taylor et al. . |
| 4,552,127 | 11/1985 | Schiff . |
| 4,681,117 | 7/1987 | Brodman et al. . |
| 4,996,989 | 3/1991 | Stundel et al. . |
| 5,006,119 | 4/1991 | Acker et al. . |
| 5,025,786 | 6/1991 | Siegel . |
| 5,114,423 | 5/1992 | Kasprzyk et al. . |
| 5,184,621 | 2/1993 | Vogel et al. . |
| 5,341,807 | 8/1994 | Nardella . |
| 5,344,398 | 9/1994 | Hara . |
| 5,368,591 | 11/1994 | Lennox et al. . |
| 5,378,238 | 1/1995 | Peters et al. ......................... 606/192 |
| 5,397,308 | 3/1995 | Ellis et al. . |
| 5,411,016 | 5/1995 | Kume et al. ......................... 606/192 |
| 5,411,478 | 5/1995 | Stillabower . |
| 5,443,470 | 8/1995 | Stern et al. . |
| 5,533,958 | 7/1996 | Wilk . |

FOREIGN PATENT DOCUMENTS

9603175A1  2/1996  WIPO .

OTHER PUBLICATIONS

Journal of the American College of Cardiology, Feb. 1989, vol. 13/No. 2/(Supplement A), Abstracts, 38th Annual Scientific Session, American College of Cardiology, Anaheim, California, Mar. 19–23, 1989.

Journal of the American College of Cardiology, Feb. 1988, vol. 11/No. 2/Supplement A), Abstracts, 37th Annual Scientific Session, American College of Cariology, Atlanta, Georgia, Mar. 27–31, 1988.

IEEE Transactions of Biomedical Engineering, vol. 39, No. 4, Apr. 1992, Electrical Impedance of Layered Atherosclerotic Plaques on Human Aortas.

IEEE Transactions on Biomedical Engineering, vol. 38, No. 5, May 1991, In Vitro Measurement and Characterization of current Density Profiles Produced by Nonrecessed, Simple Recessed, and Radially Varying recessed Stimulating Electrodes.

(List continued on next page.)

*Primary Examiner*—Guy V. Tucker
*Assistant Examiner*—Kevin Truong
*Attorney, Agent, or Firm*—Robert E. Atkinson

[57] ABSTRACT

A method of detecting a metallic stent inside a living body wherein the method includes the steps of: (1) providing a stent locator device, (2) providing a metallic stent, (3) inserting the metallic stent into the living body, (4) inserting the stent locator into the living body and (5) locating the stent with the stent locator by detecting an electrical parameter affected by the position of the stent relative to the position of the locating device. The electrical parameter may be detected with a pair of electrodes or a coil mounted to the distal end of the stent locator. The stent locator may include one or more radiopaque markers mounted on the distal end such that the position of the stent may be radiographically correlated to the position of the stent locator device. Alternatively, the stent locator may include one or more visual markers mounted on the proximal end such that the position of the stent may be visually correlated to the position of the stent locator device. The stent locator may be in the form of virtually any intraluminal device such as a guide wire, a balloon catheter, an atherectomy catheter or a stent delivery catheter. In addition, the stent may be inserted prior to, subsequent to or simultaneously with the stent locator device.

14 Claims, 9 Drawing Sheets

OTHER PUBLICATIONS

IEEE Proceedings, vol. 134, Pt.A, No. 2, Feb. 1987, Electrical Impedance Imaging.

Clin. Phys. Physiol. Meas., 1990, vol. 11, Suppl. A, 45–46, Printed in the U.K., Quantification in Impedance Imaging.

Electrical Impedance Tomography—1990, Chapter 1–Electrical Impedance Imaging, p. 1, John G. Webster; Chapter 2–Tissue Resistivity, p. 8, Ammar Rabbat; Chapter 3–Electrodes, p. 21, John G. Webster; Chapter 4–Current Generators, p. 29, Daniel J. Nowicki; Chapter 5–Voltage Measurement and Signal Demodulation, p. 43, Daniel J. Nowicki; Chapter 6–Electrical Safety, p. 58, Ali Ghahary; Chapter 13–Clinical Applications, p. 175, Sudhakar Bhat.

Impedance Measurement of Absolute Blood Flow Using an Angioplasty Cateter: A Validation Study; p. 745, From the Division of Cardiology, Department of Medicine, University of Maryland School of Medicine. Am Heart Journal 1991 121:745.

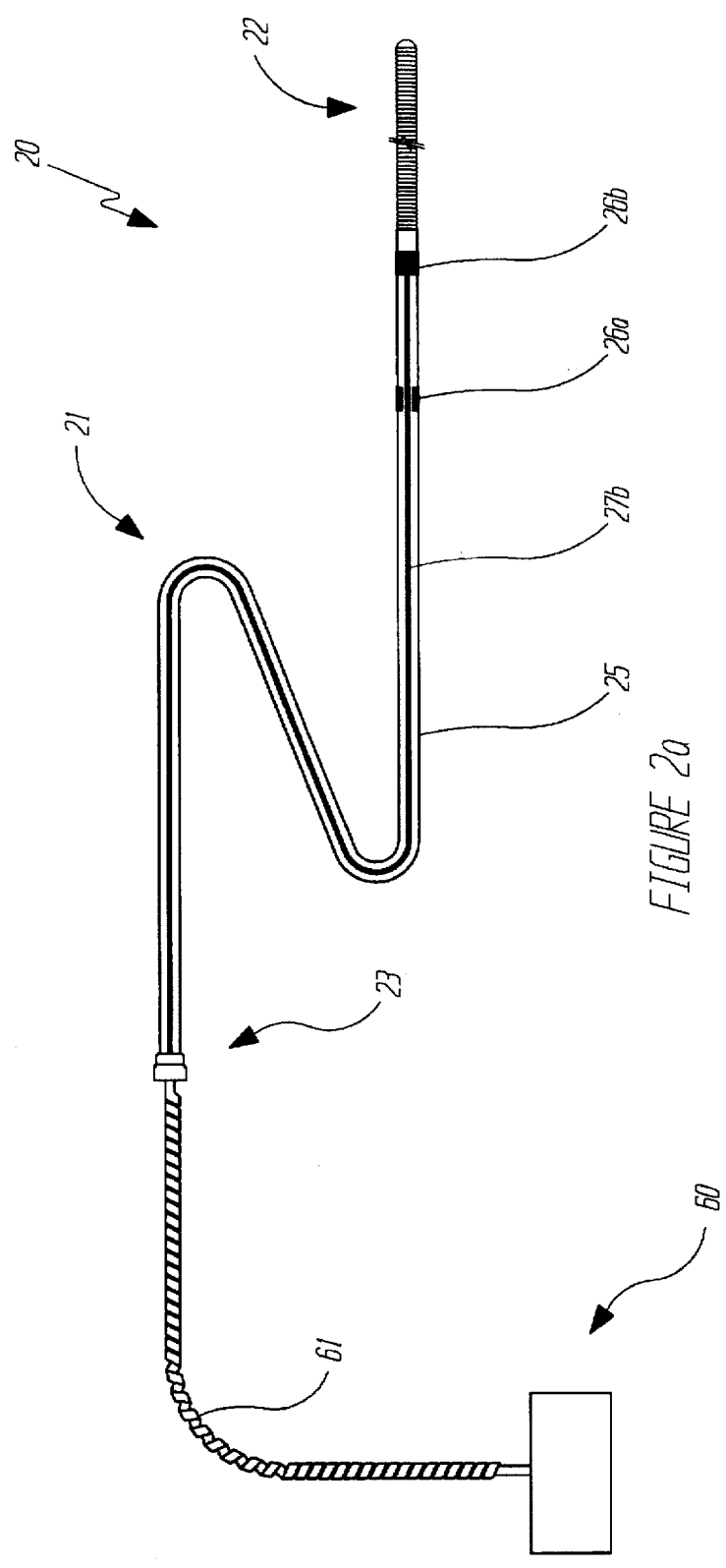
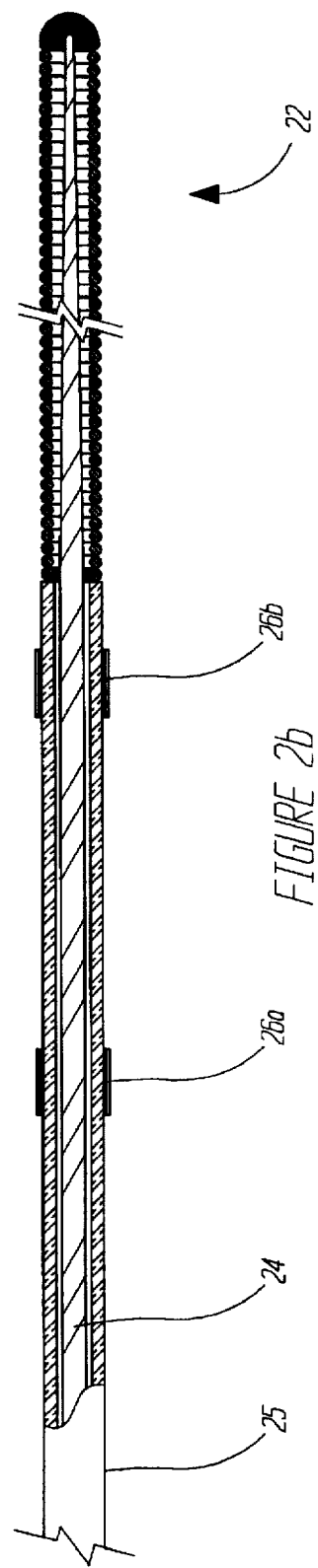
FIGURE 2a
FIGURE 2b

STENT LOCATING DEVICE

FIELD OF THE INVENTION

The present invention generally relates to intraluminal devices used to locate metallic stents inside a living body. More specifically, the present invention relates to intravascular devices used to locate metallic stents inside the vasculature of a patient. Those skilled in the art will recognize the benefits of applying the present invention to similar fields not discussed herein.

BACKGROUND OF THE INVENTION

Intravascular diseases are commonly treated by relatively non-invasive techniques such as percutaneous translumenal angioplasty (PTA) and percutaneous translumenal coronary angioplasty (PTCA). These therapeutic techniques are well known in the art and typically involve the use of a balloon catheter with a guide wire, possibly in combination with other intravascular devices. A typical balloon catheter has an elongate shaft with a balloon attached to its distal end and a manifold attached to the proximal end. In use, the balloon catheter is advanced over the guide wire such that the balloon is positioned adjacent a restriction in a diseased vessel. The balloon is then inflated and the restriction in the vessel is opened.

Vascular restrictions that have been dilated do not always remain open. The vessel may suddenly collapse shortly after dilation or the restriction may redevelop over a period of time. Acute closure (a.k.a. abrupt closure) refers to the first situation where the vessel suddenly collapses shortly after dilation. Restenosis refers to the second situation where the restriction redevelops over a period of time. Various theories have been developed to explain the cause for these incidences. For example, it is commonly believed that acute closure occurs when the vascular restriction elastically recoils after dilation. It is also belived that abrupt closure may occur as a result of an intravascular dissection or tear caused by the dilation procedure. Restenosis, by contrast, is belived to be caused by cellular proliferation over a period of time to such a degree that a stenosis or restriction is reformed in the location of the previous dilation.

Intravascular stents are now commonly used as a means to prevent abrupt closure and as a means to reduce the effects of restenosis. An example of an intravascular stent is disclosed in U.S. Pat. No. 4,733,665 to Palmaz. Palmaz '665 discloses a metallic balloon expandable stent that is currently commercially available from Johnson & Johnson. The commercially available Palmaz stent is made of stainless steel and has a wall thickness on the order of 0.0025 inches for coronary applications and 0.004 inches for other applications. Given this wall thickness and material, the commercially-available Palmaz stent is relatively difficult to locate radiographically when the the stent is inside the patient. Accordingly, it is difficult to radiographically determine if a stent is properly positioned for deployment, if a stent has been deployed in the desired position, if the stent has changed position after deployment, if the stent has restenosed or if the existance and/or location of the stent is unknown in a follow-up procedure or in an emergency situation. Due to the difficulties in radiographic visualization, the dynamic properties of the heart and intravascular blood flow, the actual position of the stent may be significantly different from the desired position. Other commercially available stents have similar radiographic visualization difficulties.

SUMMARY OF THE INVENTION

The present invention provides a device which allows the treating physician to easily determine the location of a metallic stent inside a patient, thus overcoming the disadvantages of the prior art. The present invention may be described as a method of detecting a metallic stent inside a living body wherein the method includes the steps of: (1) providing a stent locator device, (2) providing a metallic stent, (3) inserting the metallic stent into the living body, (4) inserting the stent locator into the living body and (5) locating the stent with the stent locator by detecting an electrical parameter affected by the position of the stent relative to the position of the locating device. The electrical parameter may be detected with a pair of electrodes or a coil mounted to the distal end of the stent locator. If a pair of electrodes are used, the detected electrical parameter may be conductance. If a coil is used, the detected electrical parameter may be current. The stent locator may include a signal detector which is electrically-connected to either the electrodes or the coil mounted on the distal end of the stent locator device.

The stent locator may include one or more radiopaque markers mounted on the distal end such that the position of the stent may be radiographically correlated to the position of the stent locator device. Alternatively, the stent locator may include one or more visual markers mounted on the proximal end such that the position of the stent may be visually correlated to the position of the stent locator device.

The stent locator may be in the form of virtually any intraluminal device such as a guide wire, a balloon catheter, an atherectomy catheter or a stent delivery catheter. In addition, the stent may be inserted prior to, subsequent to or simultaneously with the stent locator device.

BRIEF DESCRIPTION OF THE DRAWINGS

FIGS. 1b, 1d and 1c show detailed sectioned views of the distal portion of the stent locating device illustrated in FIG. 1a.

FIG. 2a illustrates a plan view of a stent locating device in the form of a guide wire. FIG. 2b shows a detailed sectioned view of a distal portion of the stent locating device illustrated in FIG. 2a.

DETAILED DESCRIPTION OF THE INVENTION

The following detailed description should be read with reference to the drawings in which similar parts in different drawings are numbered identically. The drawings, which are not necessarily to scale, depict exemplary embodiments and are not intended to limit the scope of the invention.

Examples of materials, dimensions and manufacturing processes are provided for selected parts. All other parts employ that which is known to those skilled in the field of the invention. Those skilled in the art will recognize that many of the examples provided have suitable alternatives which may also be utilized.

The stent locator device of the present invention may take the form of virtually any intralumenal device such as a probe, a guidewire, a balloon catheter, an atherectomy catheter, a stent delivery catheter or a stent removal catheter. In addition, if the stent locating device is in the form of an intravascular catheter, the catheter may take the form of a single-operator-exchange (SOB), fixed wire (FW) or over-the-wire (OTW) type catheter. The stent locator device of the present invention may be used in coronary, peripheral cerebral and other vascular locations in addition to urethral, biliary and other non-vascular locations. Additional features such as perfusion and drug delivery capabilities may also be incorporated into the stent locating device. For the purpose of fire following discussion, the exemplary embodiments are directed to a catheter system which is particularly suitable for coronary vascular procedures. However, with simple modifications in construction, the stent-locating device of the present invention may be used for other medical applications not fully discussed herein.

Figure 1A:
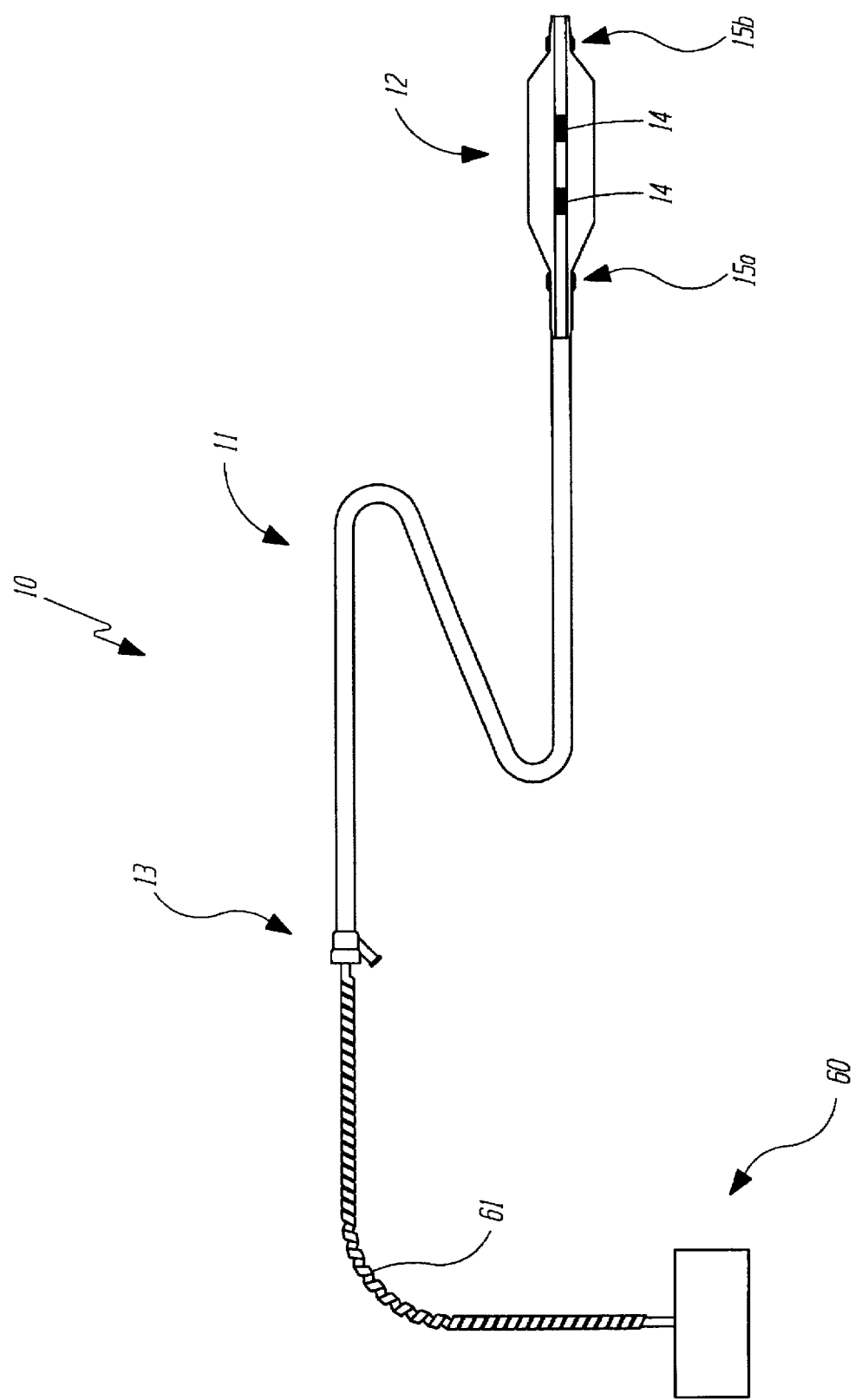
FIG. 1a illustrates a plan view of a stent locating device in the form of a balloon catheter.

Refer now to FIG. 1a which illustrates a plan view of a stent locating device 10 in the form of a balloon catheter. The stent locating device 10 includes an elongate shaft 11 with a balloon 12 connected to its distal end and a manifold assembly 13 connected to its proximal end. The manifold assembly 13 facilitates connection to an inflation device (not shown) and stent locating circuitry 60 via flexible cord 61. Manifold assembly 13 may also include additional ports for other purposes such as insertion of a guide wire, connection to infusion system, etc. Stent locating device 10 may also include a pair of radiopaque marker bands 14 connected to the portion of the shaft 11 that traverses the interior of the balloon 12. Except as discussed hereinafter, stent locating device 10 may be manufactured in a conventional manner. For example, stent locating device 10 may be manufactured as described in U.S. Pat. No. 5,338,295 to Cornelius et al., U.S. Pat. No. 5,370,616 to Keith et al., U.S. Pat. No. 5,382,234 to Cornelius et al., or U.S. Pat. No. 5,387,225 to Euteneuer et al.

Figure 1B:
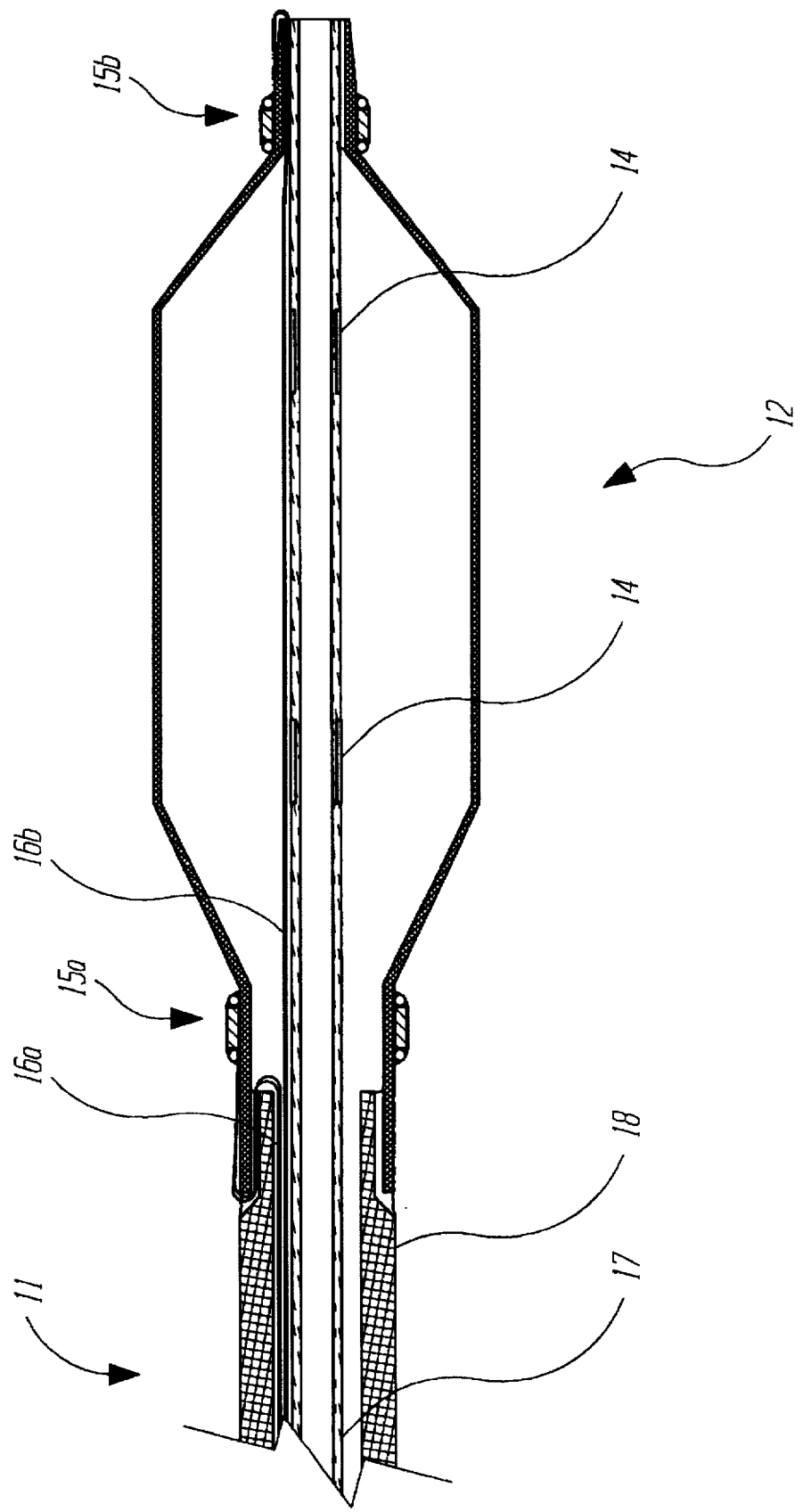

Stent locating device 10 also includes two pairs of electrodes 15a and 15b mounted on the proximal and distal waists, respectively, of the balloon 12. As best illustrated in FIG. 1b, a pair of insulated electrical leads 16a are connected to proximal electrode pair 15a. In a similar manner, a pair of insulated electrical leads 16b are connected to distal electrode pair 15b. In this particular embodiment which illustrates a coaxial OTW catheter construction, both pairs of insultated electrical leads 16a and 16b extend to the manifold assembly 13 through the elongate shaft 11 by way of the annular inflation lumen defined between inner tube 17 and outer tube 18. The proximal pair of insulated electrical leads 16a gains access to the annular inflation lumen by wrapping around the proximal edge of the proximal waist of the balloon through the adhesive bond between the outer tube 18 and the proximal waist of the balloon 12 and around the distal edge of the outer tube 18. In a similar manner, the distal pair of insulated electrical leads 16b gains access to the annular inflation lumen by winding around the distal edge of the distal waist of the balloon 12 and passing through the adhesive bond between the distal end of the inner tube 17 and the distal waist of the balloon 12.

Figure 1D:
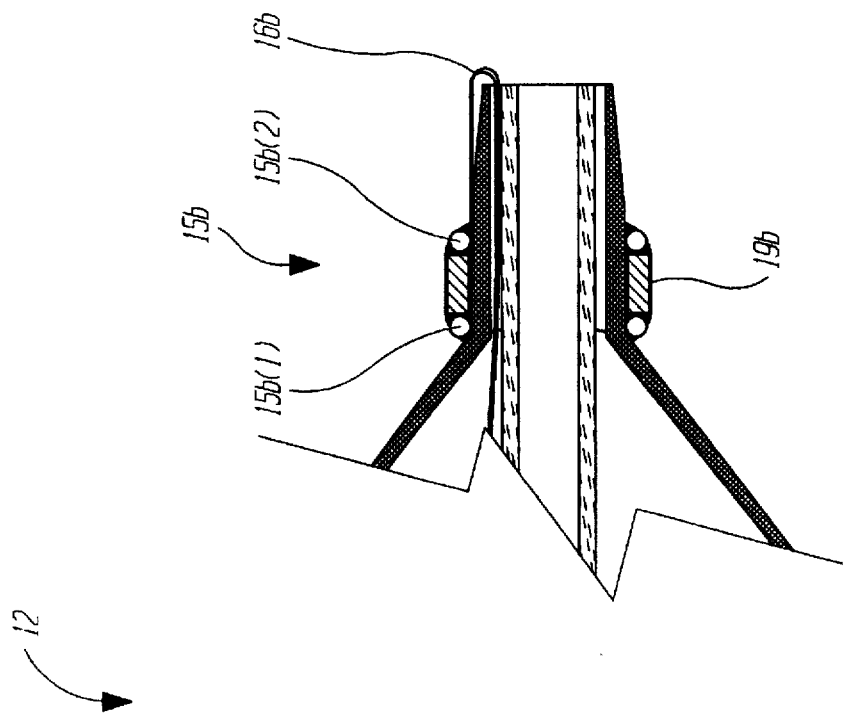
Figure 1C:
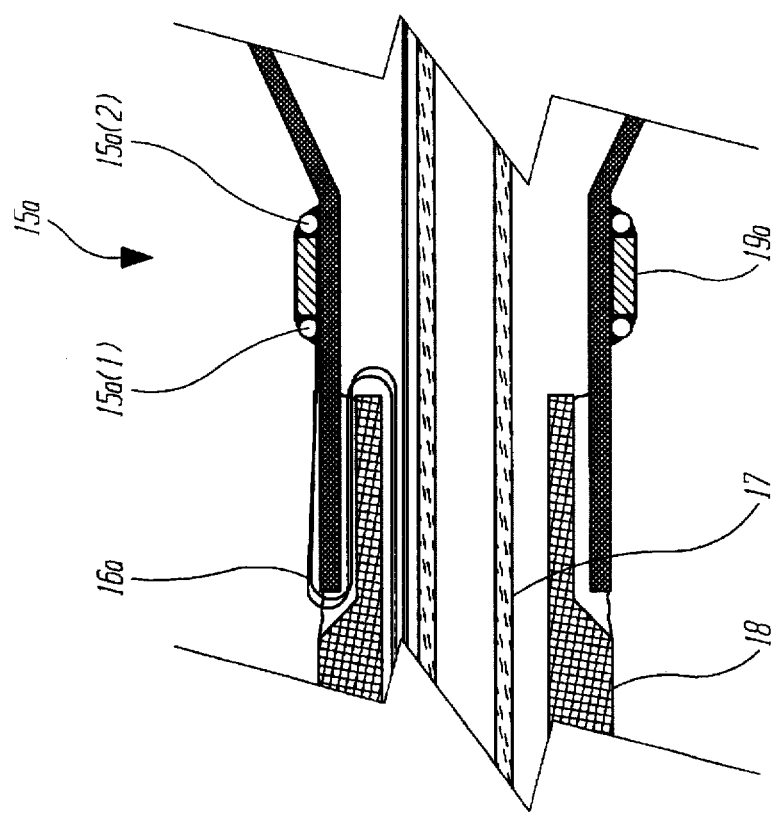

As best seen in FIGS. 1c and 1d, proximal and distal electrode pairs 15a and 15b include two discrete electrodes each. In particular, proximal electrode pair 15a includes a proximal electrode 15a(1) and a distal electrode 15a(2). In a similar manner, distal electrode 15b includes a proximal electrode 15b(1) and a distal electrode 15b(2). Each discrete electrode 15a(1), 15a(2) and 15b(1), 15b(2) is separated by an insulated spacer 19a, 19b. An adhesive coating is applied to each electrode pair 15a and 15b to secure the electrode to the balloon 12 and to provide an insulating barrier. The adhesive barrier prevents direct contact between the electrodes and the interior of the vasculature. A portion of the adhesive coating is removed such that the proximal facing portion of the proximal electrodes 15a(1), 15b(1) and the distal facing portions of the distal electrodes 15a(2), 15b(2) are exposed.

As an alternative, it is contemplated that the electrodes may have an outer surface that is exposed to enable direct contact with the vessel wall. In this embodiment, the electrodes may be used to detect the degree of stent deployment. For example, a stent that is imbedded in tissue will have a different reading than a stent that is not imbedded, due to the different electrical characteristics of metallic stents, bodily fluids and bodily tissues.

With this arrangement of electrodes, an electrical path is defined by proximal electrode 15a(1) through its immediate exterior environment to distal electrode 15a(2). In a similar manner, an electrical path is defined between proximal electrode 15b(1) through its immediate exterior environment to distal electrode 15b(2). Each of these electrical paths are separately communicated to the stent locating circuitry 60 by way of insultated electrical leads 16a, 16b and flexible cord 61. As will be discussed in more detail hereinafter, the portion of the electrical path defined by the environment immediately adjacent the electrode pairs 15a, 15b is influenced by the presence of different materials such as blood, bodily tissue and foreign materials such as intralumenal stent. Accordingly, as each electrode pair 15a and 15b passes through an electrical environment that changes, the electrical path defined by that environment will also change. The change in electrical path may be detected by stent locating circuitry 60.

Electrodes 15a(1), 15a(2) and 15b(1), 15b(2), in addition to insulated electrical leads 16a and 16b may be made of 42AWG HML silver wire which includes an insulating coating of polyimide. For biocompatability and anti-corrosion purposes, it may be preferable to use nickle-plated silver, platinum-plated silver or solid platinum. Solid platinum and platinum-plated silver may have the advantage of being more radiopaque than other suitable metallic materials. Each electrode may be wound around the balloon waist once and spaced apart by insulating spacers 19a and 19b. Insulating spacers 19a, 19b may be formed of a suitable biocompatible insulating material such as polyethylene or polytetrafluoroethylene (PTFE) having a wall thickness approximating the diameter of the wire and having a length of about 0.050 inches. The electrode pairs 15a and 15b may be adhesively secured to the balloon waists by a suitable insulating adhesive such as a UV-curable urethane adhesive.

Proximal electrode pair 15a is spaced apart from distal electrode pair 15b by approximately 2–4 millimeters less than the length of the stent to be detected. For example, if a 15-mm length stent is to be detected, the proximal electrode pair 15a may be spaced 11 to 13 mm from the distal electrode pair 15b. This arrangement permits both electrode pairs 15a and 15b to be within the length of the stent which in turn facilitates precise determination of the position of the stent.

Although a two-pair electrode system is described above, it is contemplated that a single electrode pair may also be utilized. For example, either the proximal electrode pair 15a or the distal electrode pair 15b may be used to the exclusion of the other. Having a single electrode pair mounted on the proximal end of the balloon has the advantage of not increasing catheter profile at the distal end of the catheter (which may impede the ability of the catheter to cross tight restrictions), but has the disadvantage of requiring the balloon to be advanced distally of the stent in order to determine the precise position of the stent. Utilizing a single electrode pair mounted on the distal end of the balloon has the advantage of not requiring the balloon to be advanced distally of the stent in order to determine the position of the stent, but has the disadvantage of increasing the profile of the catheter at its distal end which may impede the ability of the catheter to cross tight restrictions.

It is also contemplated that a single electrode pair may be utilized wherein the proximal electrode is mounted to the proximal waist of the balloon and the distal electrode is mounted to the distal waist of the balloon. It is believed that having an electrode pair with the proximal electrode immediately adjacent the distal electrode (e.g., 15a(1) and 15a(2)) reduces the effects of varying anatomical geometries which may adversely influence the detected electrical path.

The stent locating device 10 may be used, for example, to detect the position of a previously-inserted stent or to aid in the insertion of a stent. Accordingly, the stent locating device 10 may be inserted prior to, subsequent to, or simultaneously with a stent. For purposes of the following discussion, assume that a stent has been previously inserted into the coronary vasculature.

With the stent positioned in vivo, the stent locating device 10 may be inserted into the proper vascular path by conventional methods using conventional devices such as a guide catheter and/or a guide wire. With the stent locating device 10 positioned in vivo, a base reading is taken and the stent locating circuitry 60 is adjusted such that the signal meter 68 is calibrated to indicate a nominal inside diameter with no stent present. Once the stent locating circuitry 60 is calibrated, the stent locating device 10 is advanced until a signal is indicated on the signal meter 68. This first signal represents the distal electrode pair 15b crossing the proximal edge of the previously-inserted stent. The stent locating device 10 is then advanced until a second signal is indicated on the signal meter which represents the proximal electrode pair 15a crossing the proximal edge of the previously-inserted stent. The stent locating device 10 is then advanced slightly further until the signal from the distal electrode pair 15b drops off indicating that the distal electrode pair 15b has crossed the distal edge of the stent. At this point, the stent locating device 10 may be retracted in the proximal direction until the signal from the proximal electrode pair 15a drops off, indicating that the proximal electrode pair 15a has re-crossed the proximal edge of the stent. This iterative process is repeated until the position of the proximal and distal edges of the stent are apparent. Accordingly, the position of the previously-inserted stent is directly related to the position of the stent locating device 10. After completion of the procedure, the stent locating device 10 may be removed from the patient.

The position of the stent relative to the anatomy may be correlated by determining the position of the stent locating device 10 relative to the anatomy. The position of the stent locating device 10 relative to the anatomy may be determined by at least two different methods. For example, the position of the stent locating device 10 may be determined radiographically utilizing the radiopaque marker bands 14 mounted on the distal end of the elongate shaft 11. Since the anatomy and the radiopaque marker bands 14 are radiographically visible by conventional methods, the position of the stent is directly correlated to the position of the marker bands 14.

An alternative method utilizes visual marks (not shown) on the proximal end of the elongate shaft 11. These visual marks may be positioned at known distances from the proximal and distal electrode pairs 15a, 15b. The position of the visual marks may be compared to another previously-inserted radiographically-visible device such as a guide catheter and/or a guide wire with a known length. For example, a visual mark may be placed on the elongate shaft 11 at a distance of 110 cm from the center of the electrode pairs 15a, 15b. With this visual mark positioned adjacent the proximal end of a 100 cm guide catheter, the electrode pairs must be centered 10 cm from the distal end of the guide catheter. A plurality of visual marks may be spaced along the proximal end of the elongate shaft 11 at known incremental distances to facilitate precise determination of the position of the electrode pairs 15a and 15b.

As mentioned previously, the stent locator of the present invention may be in the form of a guide wire such as the guide wire 20 illustrated in FIGS. 2a and 2b. Stent locating guide wire 20 includes an elongate shaft 21 with an atraumatic tip 22 mounted to its distal end and a manifold assembly 23 connected to its proximal end. Atraumatic tip 22 may, for example, be in the form of a spring tip which is well-known in the art. Shaft 21 includes a core 24 manufactured by conventional methods and an outer sheath 25 disposed thereon. The outer sheath 25 has a distal end which abuts the proximal end of the atraumatic tip 22. Preferably, the outer diameter of the outer sheath 25 approximates the outer diameter of the atraumatic tip 22 to provide a smooth transition therebetween.

Outer sheath 25 includes a single pair of electrodes 26a and 26b, but may also include two or more pairs. Proximal and distal electrodes 26a and 26b electrically communicate with the stent locating circuitry 60 by way of insulated electrical leads 27a, 27b and flexible cord 61. An insulating barrier such as a polymer coating may be applied to the proximal and distal electrodes 26a and 26b to avoid direct contact with the inside of the vasculature. The proximal and distal edges of the electrodes 26a and 26b remain exposed to maintain an electrical path with the surrounding environment.

Outer sheath 25 may be made of polyimide by conventional methods. Proximal and distal electrodes 26a and 26b may be made by plating a conductive metal such as silver or gold onto the exterior of the sheath 25 and etching away the unneeded portions of the coating. Alternatively, the outer sheath 25 may masked or screened such that a metallic coating is applied only in the desired locations. The proximal electrode 26a may be formed in a semicircular geometry to allow passage of the distal electrical lead 27b. Electrical leads 27a and 27b may be formed in the same manner as the proximal and distal electrodes 26a and 26b.

The stent locating device 20 may be used in substantially the same way as the stent locating device 10. Note, however, that the stent locating device 20 shows only a single pair of electrodes whereas the stent locating device 10 shows two pairs of electrodes. As mentioned previously, the number and arrangement of electrodes may vary, depending on the competing factors considered to be most desirable.

Figure 3:
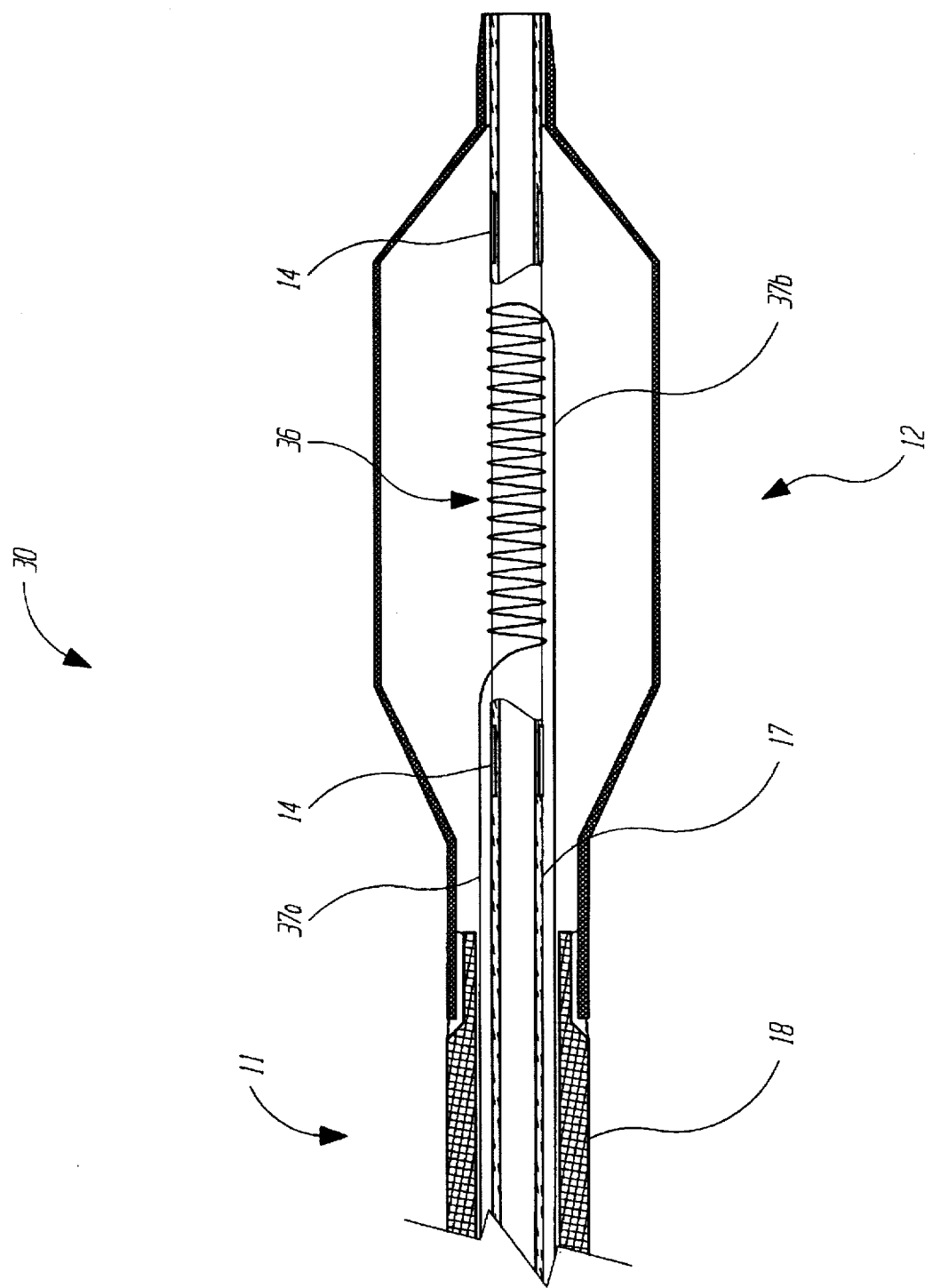
FIG. 3 illustrates a partial longitudinal cross-sectioned view of an alternative stent locating device in the form of a balloon catheter.

Refer now to FIG. 3 which illustrates an alternative electrode system. Stent locating device 30 is made and used the same as stent locating device 10 with the following exceptions. Stent locating device 30 includes a coil 36 wound about the inner tube 17 under the balloon 12. Marker bands 14 are positioned equi-distant either side of the coil 36. The coil 36 is electrically connected to stent locating circuitry 60 by way of insulated electrical leads 37a, 37b and flexible cable 61.

The principles of operation of stent locating device 30 differ from the principles discussed with reference to stent locating device 10 in that a stent is located by detecting changes in an electrical field surrounding the coil 36. The principles of operation of stent locating device 10 are based in part on changes in electrical paths versus stent locating device 30 which are based in part on changes in electrical fields. In particular, as a metallic object moves past coil 36, an electromotive force is generated which may be detected by suitable circuitry. Although only one coil is illustrated on the stent locating device 30, two or more coils may be utilized depending on the competing factors found most desirable.

Preferably, coil 36 is made of about to 100 to 500 turns of AWG 50 insulated wire such as silver, copper or platinum having a length of about 0.1 to 0.5 inches. One or more coils may be used and the either a single layer or multiple layers may be utilized.

It is contemplated that a single coil may be used in combination with an external electrode connected to the patient. In this embodiment, the capacitance will change as a function of the presence or absence of a stent.

It is further contemplated that a single coil may be used in combination with an external antenna with a radio transmitter connected to the coil (internal antenna) and a receiver connected to the external antenna. In this embodiment, the electromagnetic signal will change as a function of the presence or absence of a stent which interferes with radio waves.

Figure 4:
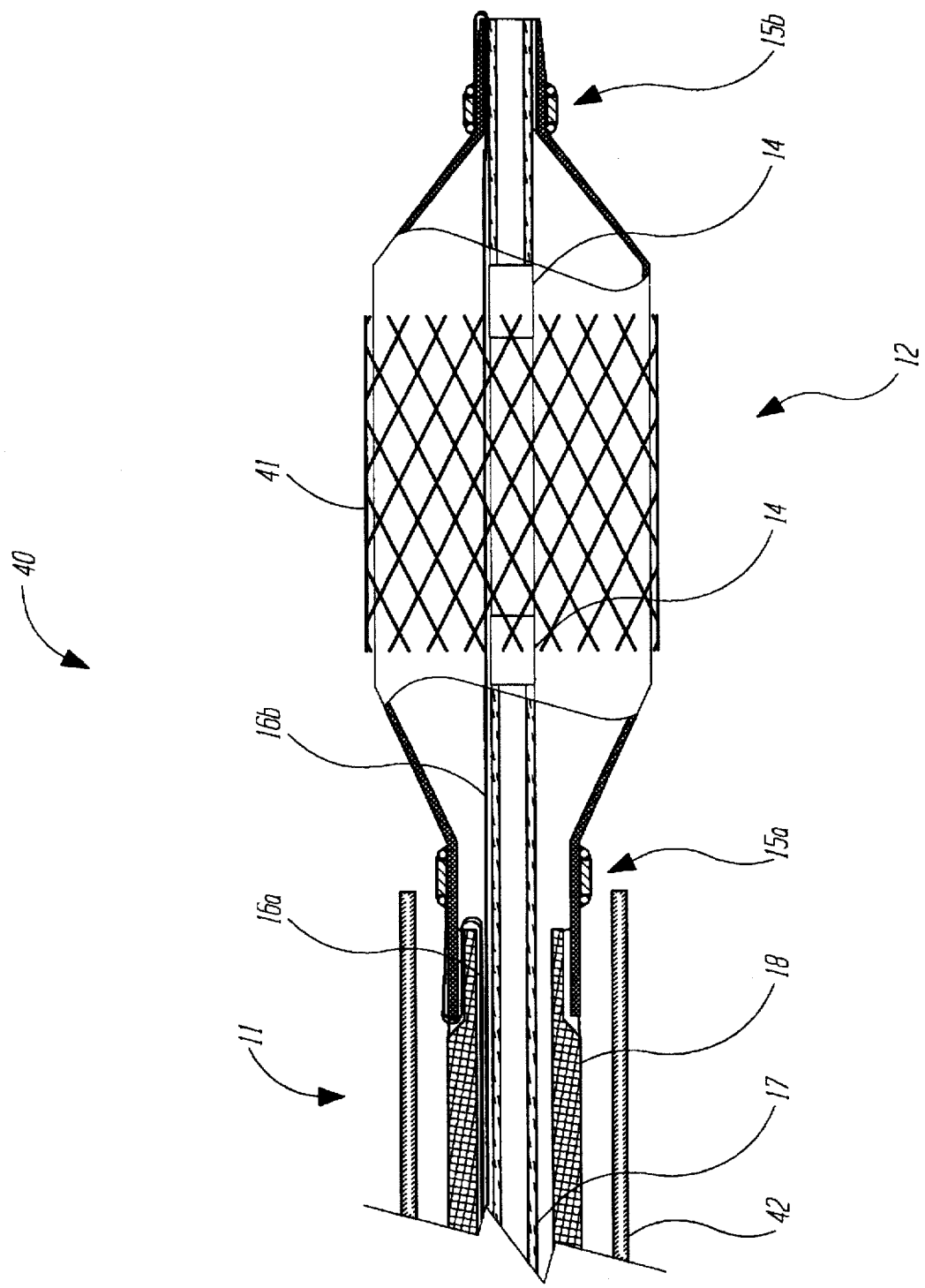
FIG. 4 illustrates a partial longitudinal cross-sectioned view of a stent-locating device in the form of a stent delivery catheter.

Refer now to FIG. 4 which illustrates a stent locating device 40 in the form of a stent delivery device. The stent delivery device is manufactured and used in the same way as stent locating device 10 with the following exceptions. Stent locating device 40 includes a stent 41 mounted on the balloon 12 (shown in the expanded state). Stent locating device 40 also includes a retractable sheath 42 (shown in a retracted position) which secures the stent 41 to the balloon 12 until the stent 41 is ready for deployment. An example of a similar stent delivery system (with exception of the stent locating features) is disclosed in U.S. Pat. No. 5,092,877 to Pinchuk.

Figure 5:
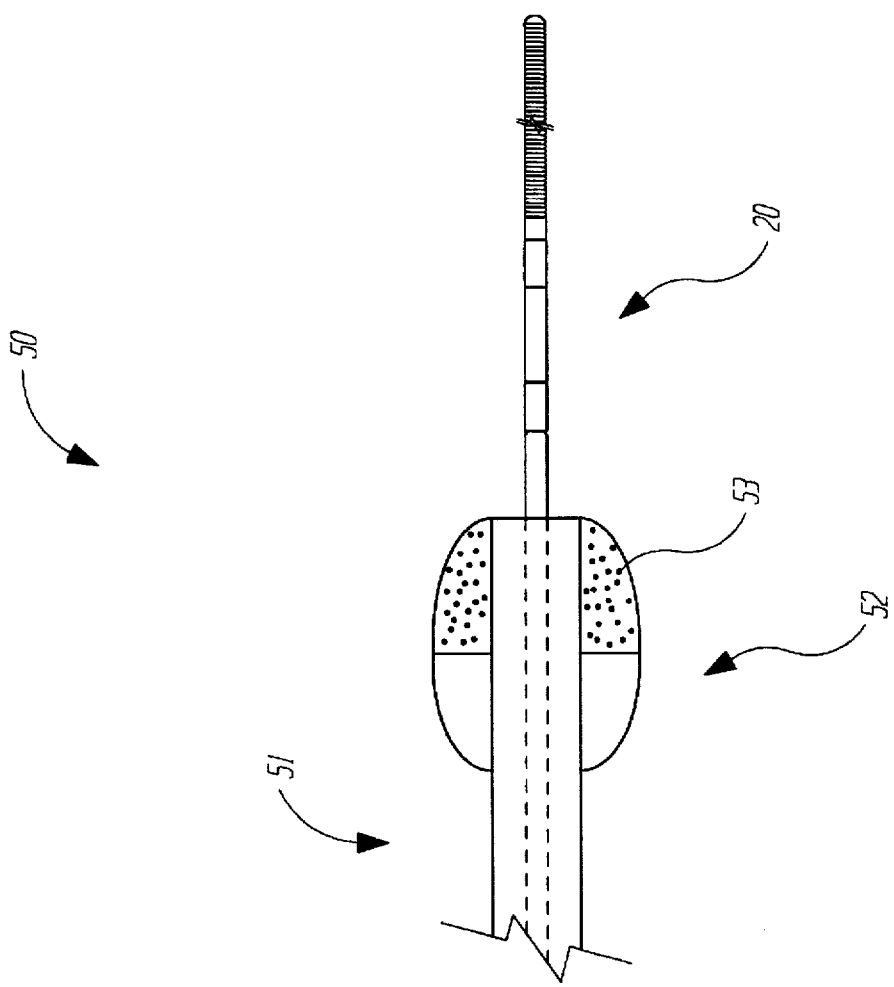
FIG. 5 illustrates a plan view of a stent-locating device in the form of an atherectomy catheter.

Refer now to FIG. 5 which shows a stent locating device 50 in the form of an atherectomy catheter. Stent locating device 50 includes a rotational cutter 52 mounted on the distal end of a drive shaft 51. Rotational cutter 52 may include an abrasive coating 53 to facilitate differential cutting of intravascular tissue. Drive shaft 51 is hollow such that a guide wire 20 may be inserted therein. Guide wire 20 may be substantially as described with reference to FIGS. 2a and 2b. An example of a similar atherectomy device (with exception of the stent locating features) is disclosed in U.S. Pat. No. 4,445,509 to Auth.

Figure 6:
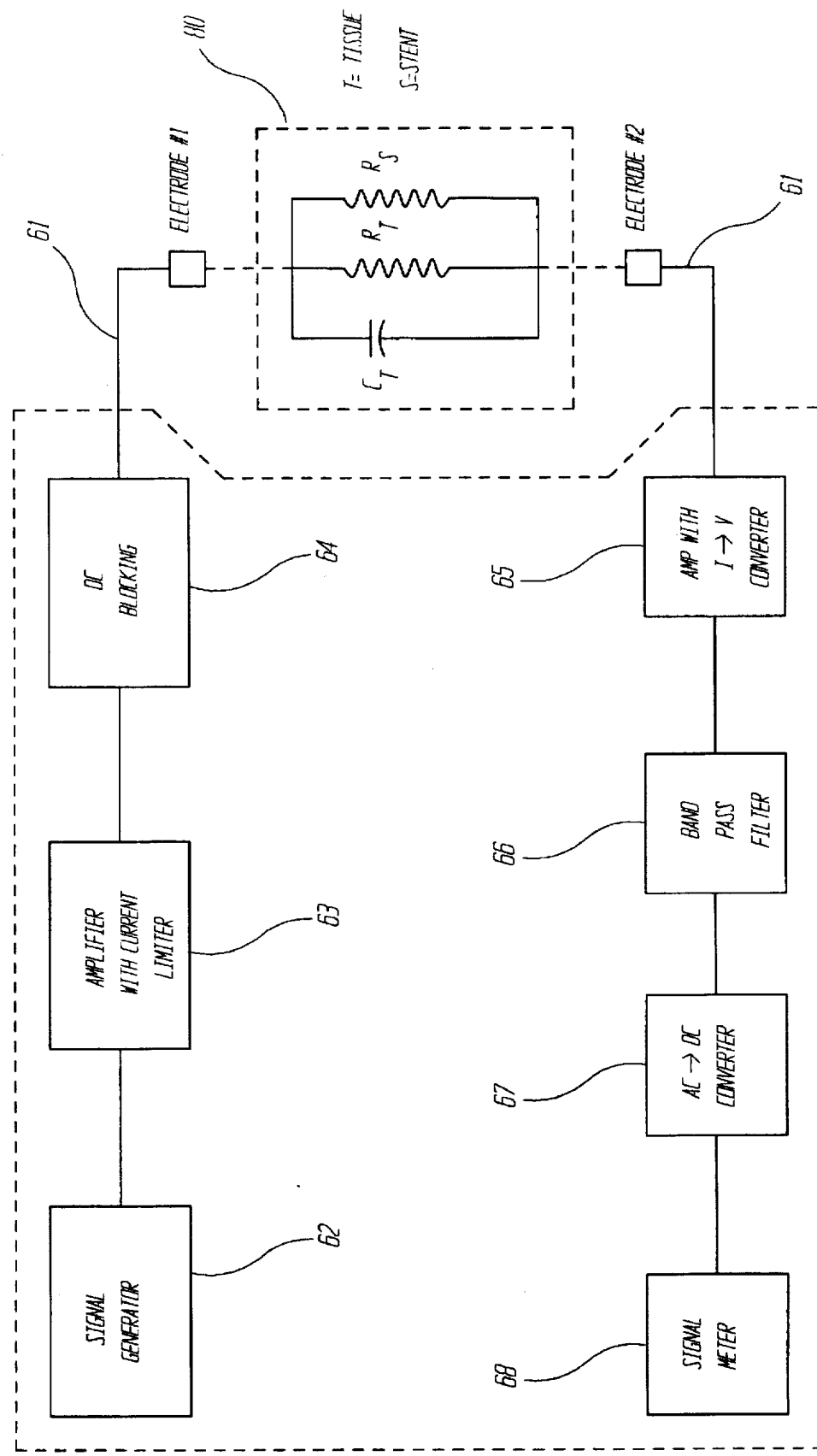
FIG. 6 illustrates a block diagram of a suitable circuit for use in conjunction with the stent-locating device of the present invention.

Refer now to FIG. 6 which illustrates a block diagram of the stent locating circuitry 60 as used with a single pair of electrodes. If more than one pair of electrodes are used, an additional stent locating circuit may be used or a switch may be provided to alternate between pairs of electrodes. The stent locating circuitry includes a flexible cord 61 which is electrically connected to a pair of electrodes designated electrode #1 and electrode #2.

The electrical environment 80 in which the electrodes are used is schematically represented as a parallel RC circuit wherein $R_s$ is the resistance of the stent, $R_t$ is the resistance of the surrounding tissue and $C_t$ is the capacitance of the surrounding tissue.

Stent locating circuitry 60 includes a signal generator 62 which generates an AC signal on the order of 0.1 to 10 MHz. Signal generator 62 is connected to an amplifier 63 which includes a current limiter. Amp 63 is connected to a DC blocker 64 which prevents DC current from passing through to the electrodes (in order to avoid inducement of adverse cardiac currents). The DC blocker 64 is connected to a first electrode via flexible cord 61. The opposite electrode is also connected to flexible cord 61, which in turn is connected to amp 65 which includes a current-to-voltage converter. Amp 65 is connected to band pass filter 66 which freely passes currents having specified frequencies and highly attenuates currents with frequencies outside the nominal limits. Band pass filter 66 is connected to an AC-to-DC converter 67, which in turn is connected to a signal meter 68. Signal meter 68 preferably includes a series of LED's having three different colors. For example, green may be used to indicate a base line signal which corresponds to the nominal inside diameter of the intralumenal path. Yellow may be used to indicate a damped signal which corresponds to a vascular restriction. The damped signal occurs in a vascular restriction because blood is generally more conductive than abnormal deposits. A damped signal may also indicate a gap within a stent such as an articulated stent. Red may be used to indicate a peak signal, representing a fully-expanded stent. The peak signal occurs in an expanded stent because a stent is generally more conductive than both blood and abnormal deposits.

Figure 7:
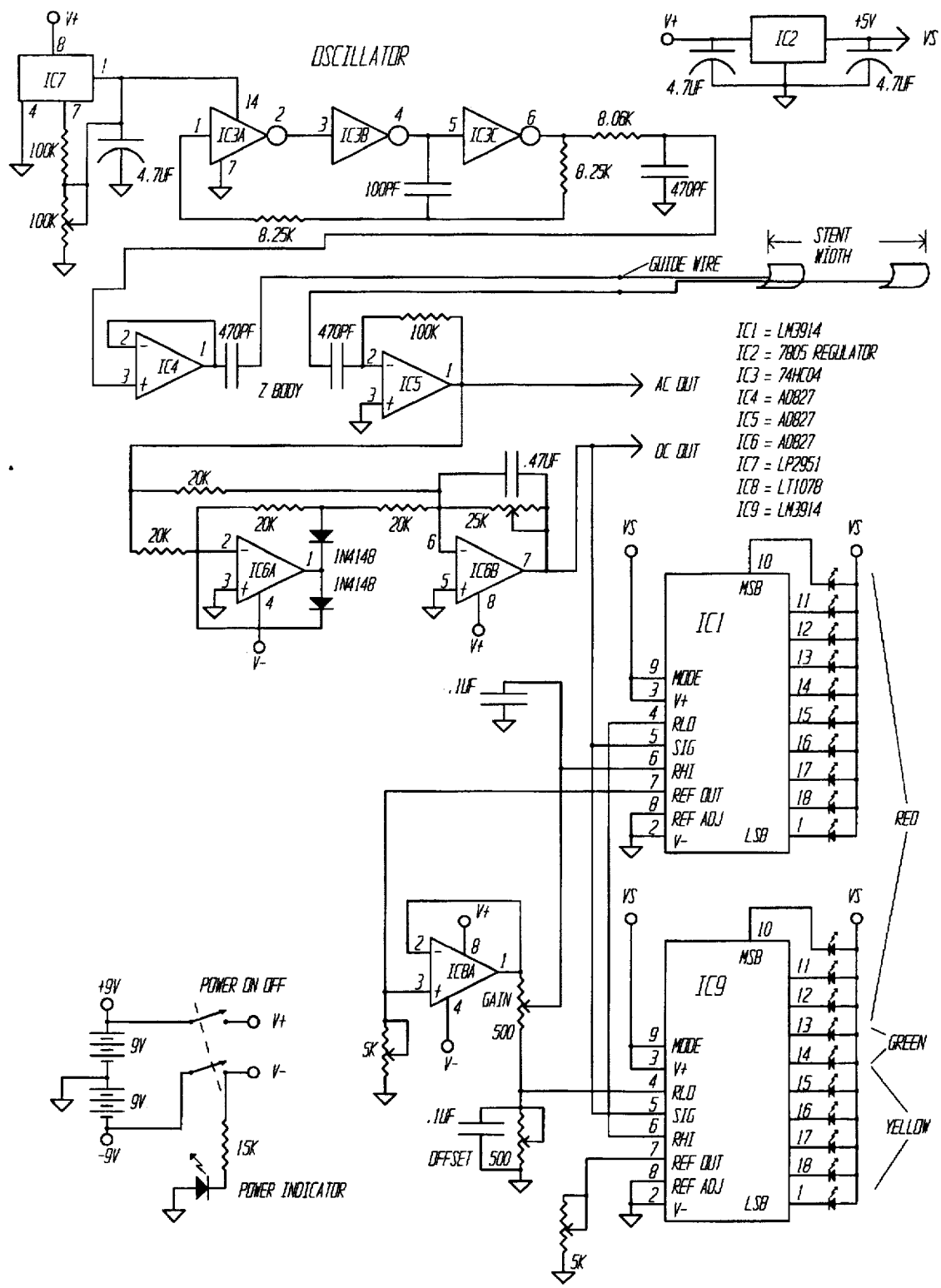
FIG. 7 illustrates a schematic diagram of a suitable circuit for use in conjunction with the stent-locating device of the present invention.

FIG. 7 illustrates a schematic diagram of a particularly suitable circuit for use in combination with the stent locating device of the present invention.

While the specification describes the preferred embodiments, those skilled in the art will appreciate the scope and spirit of the invention with reference to the appended claims.

What is claimed is:

1. A method of detecting a metallic stent inside a living body, comprising the steps of:
    (i) providing a stent locator device having a proximal end, a distal end and a pair of electrodes mounted on the distal end;
    (ii) providing a metallic stent;
    (iii) inserting the metallic stent inside the living body;
    (iv) inserting the stent locator inside the living body; and
    (v) locating the stent with the stent locator by detecting an electrical parameter when the electrodes on the stent locator are positioned adjacent the stent.

2. A method of detecting a metallic stent inside a living body as in claim 1, wherein the stent locator includes a signal detector electrically connected to the electrodes.

3. A method of detecting a metallic stent inside a living body as in claim 2, wherein the detected electrical parameter is conduction.

4. A method of detecting a metallic stent inside a living body as in claim 3, wherein the stent locator device includes at least one radiopaque marker mounted on the distal end.

5. A method of detecting a metallic stent inside a living body as in claim 4, further comprising the step of:
(vi) radiographically locating the radiopaque marker on the stent locator to determine the position of the stent.

6. A method of detecting a metallic stent inside a living body as in claim 3, wherein the stent locator device includes at least one visual marker mounted on the proximal end.

7. A method of detecting a metallic stent inside a living body as in claim 6, further comprising the step of:
(vi) visually locating the visual marker on the stent locator to determine the position of the stent.

8. A method of detecting a metallic stent inside a living body as in claim 3, wherein the stent locator is a guide wire.

9. A method of detecting a metallic stent inside a living body as in claim 3, wherein the stent locator is a balloon catheter.

10. A method of detecting a metallic stent inside a living body as in claim 3, wherein the stent locator is an atherectomy catheter.

11. A method of detecting a metallic stent inside a living body as in claim 3, wherein the stent locator is a stent delivery catheter.

12. A method of detecting a metallic stent inside a living body as in claim 3, wherein the stent is inserted prior to the stent locator.

13. A method of detecting a metallic stent inside a living body as in claim 3, wherein the stent locator is inserted prior to the stent.

14. A method of detecting a metallic stent inside a living body as in claim 3, wherein the stent and the stent locator are inserted simultaneously.

* * * * *

UNITED STATES PATENT AND TRADEMARK OFFICE
CERTIFICATE OF CORRECTION

PATENT NO. : 5,665,103

DATED : September 9, 1997

INVENTOR(S) : LAFONTAINE et al.

It is certified that error appears in the above-identified patent and that said Letters Patent is hereby corrected as shown below:

At column 3, line 10, "(SOB)" should be --(SOE)--; at line 17, "fire" should be --the--.

Signed and Sealed this

Fifteenth Day of December, 1998

Attest:

BRUCE LEHMAN

*Attesting Officer*  *Commissioner of Patents and Trademarks*